United States Patent [19]

Insana et al.

[11] Patent Number: 4,817,015
[45] Date of Patent: Mar. 28, 1989

[54] HIGH SPEED TEXTURE DISCRIMINATOR FOR ULTRASONIC IMAGING

[75] Inventors: Michael F. Insana; Stephen W. Smith, both of Rockville; David G. Brown, Derwood; Robert F. Wagner, Gaithersburg, all of Md.

[73] Assignee: The United States Government as represented by the Secretary of the Health and Human Services, Washington, D.C.

[21] Appl. No.: 798,930

[22] Filed: Nov. 18, 1985

[51] Int. Cl.$^4$ ............... A61B 10/00; G06F 15/20; G01N 29/04
[52] U.S. Cl. ............... 364/507; 364/413.25; 128/660.01; 73/599; 73/602
[58] Field of Search ........... 364/550, 551, 554, 507, 364/414, 415, 416, 413; 128/660; 73/599, 602, 606

[56] References Cited

U.S. PATENT DOCUMENTS

| | | | |
|---|---|---|---|
| 4,202,215 | 5/1980 | Meyer | 73/599 |
| 4,261,040 | 4/1981 | Weidman et al. | 364/554 |
| 4,283,953 | 8/1981 | Plona | 73/589 |
| 4,327,588 | 5/1982 | North | 73/599 |
| 4,389,893 | 6/1983 | Ophir et al. | 73/599 |
| 4,412,544 | 11/1983 | Beretsky et al. | 128/660 |
| 4,441,368 | 4/1984 | Flax | 73/599 |
| 4,452,082 | 6/1984 | Miwa | 73/602 |
| 4,453,550 | 6/1984 | Flax | 128/660 |
| 4,475,396 | 10/1984 | Flax et al. | 73/599 |
| 4,475,398 | 10/1984 | Tjornehoj et al. | 73/599 |
| 4,509,524 | 4/1985 | Miwa | 73/599 |
| 4,511,984 | 4/1985 | Sumino et al. | 364/415 |
| 4,512,195 | 4/1985 | Miwa et al. | 73/602 |
| 4,515,163 | 5/1985 | Flax et al. | 128/660 |
| 4,539,848 | 9/1985 | Takafuji et al. | 73/599 |
| 4,542,744 | 9/1985 | Barnes et al. | 128/660 |
| 4,597,292 | 7/1986 | Fujii et al. | 73/599 |
| 4,644,510 | 2/1987 | Fujii | 73/599 |
| 4,646,748 | 3/1987 | Fujii et al. | 128/660 |

OTHER PUBLICATIONS

R. Kuc, M. Schwartz and L. von Micsky, Parametic Estimation of the Acoustic Attenuation Coefficient Slope for Soft Tissues, IEEE Ultrasonics Symposium Proceedings, IEEE Ct. #76Ch, 1120-5SU, 44-47, Mar. 1977.

R. Kuc, Clinical Application of an Ultrasound Attenuation Coefficient Estimation Technique for Liver Pathology, IEEE Trans. Biomed. Eng. BME-27, Jan. 1980.

J. Ophir, R. E. McWhirt, N. F. Maklad, and P. M. Jaeger, A Narrow-Band Pulse-Echo Technique for in vivo Ultrasonic Attenuation Estimation, IEEE Trans. Biomed. Eng. BVE-32, 205-212, Mar. 1985.

S. W. Flax, N. J. Pelc, G. H. Glover, F. D. Gutmann, M. McLachlan, Spectral Characterization and Attenuation Measurements in Ultrasound, Ultrasound Imaging, 5, 95-116, 1983.

L. L. Fellingham-Joynt, A Stochastic Approach to Ultrasonic Tissue Characterization, Standord Elect. Lab. Report G557-4, Jun. 1979.

D. J. Skorton, H. E. Melton, N. G. Panadian, J. Nichols, S. Koyanagi, M. L. Marcus, S. M. Collins, R. E. Kerber, Detection of Acute Myocardial Infarction in Closed Chest Dogs by Analysis of Two-Dimensional Echocardiographic Gray Level Distributions, Circ. Res. 52, 36, Jan. 1983.

(List continued on next page.)

Primary Examiner—Parshotam S. Lall
Assistant Examiner—Brian M. Mattson
Attorney, Agent, or Firm—Browdy and Neimark

[57] ABSTRACT

Tissue signatures are obtained from first and second order statistics of an image texture to discriminate between different normal tissues and to detect abnormal conditions. These signatures describe intrinsic backscatter properties of the tissue imaged, and are used as the basis of an automatic tissue characterization algorithm. A device for on-line classifying of the texture of an image measures a total of four first and second order statistical properties of echo signals of a region of interest (ROI) selected by an operator, the echo signals being contained in an image memory. These can be used to obtain the tissue signatures, to detect low contrast lesions by machine, and to produce parametric images.

20 Claims, 5 Drawing Sheets

OTHER PUBLICATIONS

S. Green, L. Joynt, P. J. Fitzgerald, D. Rubenson, R. L. Popp, In vivo Ultrasonic Tissue Characterization of Human Intracardiac Masses, Am. J. Cardiol. 51, 231, Jan. 1983.

Shimadzu, Ultrasonic Linear Array Scanner, Model SDL-150, 1985.

M. Matsumoto, T. Shimazu, M. Fujiwara, H. Nishioka, T. Matsuyama, K. Yasui, Y. Hamanaka, M. Inoue, H. Abe and H. Miwa, Ultrasonic Tissue Characterization of Infarcted Myocardium Employing Cepstral Analysis, WFUMB, 512, 1985.

F. G. Sommer, L. Fellingham-Joynt, B. A. Carroll, and A. Macovski, Ultrasonic Characterization of Abdominal Tissue via Digital Analysis of Backscattered Waveforms, Radiology, 141, 811–817, Dec. 1981.

L. L. Fellingham and F. G. Sommer, Ultrasonic Characterization of Tissue Structure in the vivo Human Liver and Spleen, IEEE Trans Sonics and Ultras. SU-31, 418–428, Jul. 1984.

D. L. King, F. L. Lizzi, E. J. Feleppa, P. M. Wai, M. M. Yaremko, M. C. Rorke, J. Hebst, Focal and Diffuse Liver Disease Studied by Quantitive Microstructural Sonography, Radiology, 155, 457–462, May 1985.

F. J. Lizzi, M. Greenbaum, E. J. Feleppa, M. Elbaum, and D. J. Coleman, Theorectical Framework for Spectrum Analysis in Ultrasonic Tissue Characterization, J. Acoust. Soc. Amer., 73, 1366–1373, Apr. 1983.

U. Raeth, D. Schlaps, B. Limberg, I. Zung, A. Lorenz, G. von Kaick, W. J. Lorenz, B. Kommerell, Diagnostic Accuracy of Computerized B-Scan Texture Analysis and Conventional Ultrasonography in Diffuse Parenchymal and Malignant Liver Disease, J. Clin. Ultra. 13, 87–99, Feb. 1985.

R. W. Wagner, M. F. Insana, D. G. Brown, Unified Approach to the Detection and Classification of Speckle texture in Diagnostic Ultrasound, Proc. Soc. Photo-opt. Engrs., Aug. 1985.

M. F. Insana, R. F. Wagner, B. S. Garra, D. G. Brown, and T. S. Shawker, Analysis of Ultrasound Image Texture via Generalized Rician Statistics, Proc. Soc. Photo-opt Engrs., Aug. 1985.

J. W. Goodman, Statistical Properties of Laser Speckle Patterns, in Laser Speckle and Related Phenomena, J. C. Dainty, ed., 9–75, Berlin: Springer-Verlag, 1975.

R. F. Wagner, S. W. Smith, J. M. Sandrik, and H. Lopez, Statistics of Speckle in Ultrasound B-Scans, IEEE Trans sonics and Ultrason. SU-30, 156–163, May 1983.

HIGH SPEED TEXTURE DISCRIMINATOR FOR ULTRASONIC IMAGING

FIELD OF THE INVENTION

The present invention relates to tissue characterization of ultrasound images, and, more particularly, to a high speed texture discriminator that measures first and second order statistical properties of echo signals.

BACKGROUND OF THE INVENTION

In many medical applications, ultrasonic imaging has provided a low cost and effective method of diagnosing disease. B-scan images are two-dimensional maps of acoustic echoes from tissue components. These images have a textured or speckled appearance that is characteristic of the interaction between the fairly coherent pulse transmitted and the scattering sites in tissues. Texture is often viewed as image noise which hinders the detection and interpretation of such signals of soft tissue lesions. However, with appropriate statistical analysis, quantitative information specific to imaging performance and tissue characteristics can be extracted from the image texture.

Detecting the presence of disease in tissue parenchyma on a quantitative, operator independent basis is the objective of tissue characterization methods. Toward this goal, many ultrasonic tissue characterization techniques have been proposed. The success of these methods depends, however, on how well measured acoustic properties or signal parameters correlate with disease states. The most widely studied characterization method is measurement of ultrasonic attenuation, which represents the total lineal loss of acoustic energy for ultrasound propagating through tissue. A number of spectral and time domain techniques have been proposed. Two attenuation techniques have been implemented in prototype commercial clinical B-scanning hardware.

Several patents, such as U.S. Pat. Nos. 4,475,397 and 4,515,613, have disclosed devices for determining the attenuation coefficient of tissue from zero crossings to frequency spectrum of reflected waves. Others like Miwa in U.S. Pat. No. 4,509,524 determine the attenuation coefficient of the tissue by comparing reflected waves of different frequencies of the tissue with a reference medium. The Flax et al U.S. Pat. No. 4,475,396 discloses a time based method of determining attenuation coefficient.

Stochastic methods for analyzing image texture have became a topic of increasing scientific interest because the results can be directly related to observable image characteristics and physical scattering properties. Several research groups have conducted off-line studies of the moments of first order statistics such as mean, variance and kurtosis as measures of tissue characterization. A common limitation of these studies is that the analysis is performed off-line with long turnaround times, diminishing effectiveness in any proposed clinical environment application.

Fellingham and Sommer (Ultrasonic Characterization of Tissue Structure in the In Vivo Liver and Spleen IEEE Transaction on sonics and ultrasonics, Vol. SU-31, No. 4, July 1984) describe measurement of means scatterer spacing as a tool for tissue characterization.

In all the above systems there is either insufficient information for tissue characterization and discrimination, or there is not present a strong physical-statistical basis for the analysis of tissue images, specifically for discrimination in low contrast media.

Thus, in spite of the great need which has existed for many years, and the very great activity among researchers and practical workers in the art, there has not previously been provided a satisfactory system for rapidly detecting on-line the presence of disease in tissue parenchyma on a quantitative, operator independent basis, using ultrasonic imaging.

SUMMARY OF THE INVENTION

Accordingly, it is an object of the present invention to overcome deficiencies in the prior art, such as indicated above.

It is another object of the invention to provide improved ultrasonic imaging information.

It is a further object to detect the presence of disease in tissue parenchyma on a quantitative, operator independent basis.

It is yet another object to provide an improved method of tissue characterization that uses, in addition to the mean spacing of periodic tissue scatterers, intrinsic backscatter properties of tissues which can be estimated from the image statistics.

Still another object of the present invention is to provide a device for high speed on-line implementation of the above method which is adaptable to currently in-use ultrasound imaging devices.

A further object of the present invention is to provide a device for detecting low contrast lesions, and another object is to provide a device for producing parametric images.

BRIEF DESCRIPTION OF THE DRAWINGS

Other objects and the nature and advantages of the instant invention will be more apparent from the following detailed description of the invention taken in conjunction with the drawing, wherein.

DETAILED DESCRIPTION OF EMBODIMENTS

Studies over the years have shown that tissue scatterers vary in size and shape, and that different biological structures have varying degrees of spatial order. The simplest biological scattering medium is unclotted blood which is completely disordered, consisting of randomly distributed Rayleigh scatterers. At the other extreme is the very complex anisotropic structure of skeletal muscle tissue. This tissue is highly ordered, with nearly periodic scatterers that repeat over a long range.

The organization of scattering structures for most media fall somewhere in between blood and skeletal muscle, and it is for these structures that the problem of detecting such organized structure by means of ultrasonic imaging has been so difficult.

Backscatter properties can be derived from the intensity image, $I(z,\theta)$, which is defined as the squared envelope of the complex ultrasonic echo signal, $g(z,\theta)$, or $T=|g|^2$. Here z is the range direction and $\theta$ is the sector angle in a sector B-scan image or the scan direction in a retangular format. The echo signal g is the sum of scattering from a diffuse (incoherent) component, $g_r+ig_i$, and a specular (coherent) component $\hat{R}(z,\theta)$ from scattering sites with semi-periodic, long range order, a function of position. The average intensity autocorrelation function, $R_I(\Delta z)$ for a region of interest (ROI) in the intensity image is calculated along the range direction. The ROI is chosen so that the effect of specular scatterers such as blood vessels and organ surfaces can be assumed to be negligible.

We have now derived the expression for $R_I(\Delta z)$ assuming a Rician probability distribution function (pdf):

$$R_I(\Delta z) = <I(z_1)I(z_2)> = I_d^2(1+|\rho|^2)+2I_d\overline{I_s}+ <I_s(z_1)^*I_s(z_2)>+2I_d\rho<\hat{R}(z_1)^*\hat{R}(z_2)>. \quad (1)$$

$I_d$ = diffuse or average incoherent backscatter intensity from ROI, $\overline{I_s}$ = the average specular backscatter intensity and $\overline{I} = I_d + \overline{I_s}, \rho$ = the complex coherence factor; and, for stationary data, the last two terms can be interpreted as average autocorrelations of $I_s$ and R averaged over $\theta$.

To form the features space, in the present invention the following three values of $R_I(\Delta z)$ at the lags $\Delta z$ are defined, recognizing that the mean square $\overline{I^2} = t$ and squared mean $(\overline{I})^2 = b$ may be obtained by setting $\rho = 1$ and $\rho = 0$, respectively, in Eq. 1.

$$t = R_I(0) = 2I_d^2 + 4I_d\overline{I_s} + \overline{I_s^2} \quad (2)$$

$$p = R_I(\overline{d}) = I_d^2 + 2I_d\overline{I_s}30\ \overline{i_s^2} \quad (3)$$

$$b = R_I(\Delta z >> \overline{d}) = (I_d + \overline{I_s})^2. \quad (4)$$

Figure 1:
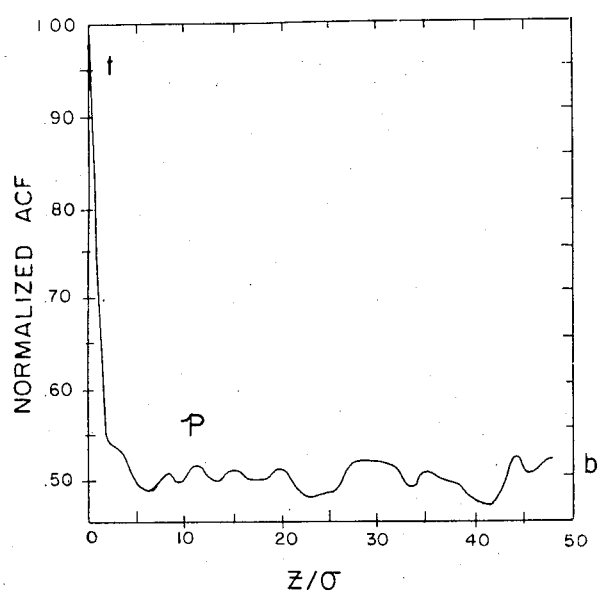
FIG. 1 is a graph which shows the average autocorrelation function in the range direction, specifying t, p, and b, three parameters of texture discrimination.

There is also a fourth parameter $\overline{d}$, the average spacing between resolvable specular scatterers, which may be found from the lag value separating correlation peaks in $R_I(\Delta z)$ (FIG. 1). It is however, more easily measured from peaks in the power spectrum.

Through simple quadratic relations, the parameters t, p, and b are related to the scattering properties of the imaged tissues.

$$I_d = (b)^{\frac{1}{2}} - (b-t+p)^{\frac{1}{2}} \quad (5)$$

$$\overline{I_s} = (b-t+p)^{\frac{1}{2}} \quad (6)$$

$$\text{var}^{\frac{1}{2}}(I_s) = (p-b)^{\frac{1}{2}} \quad (7)$$

Here t is the second moment of the intensity image and b is the square of the first moment. Thus, the parameter b is the squared mean of the intensity image, a measure of mean ultrasound backscatter intensity in the ROI. The parameter t−b is the variance in the intensity image from both random and specular scatters i.e. the Rician noise variance. If the tissue contains no specular scatterers or if the spacing between the specular scatterers is closer than the resolution of the imaging system, then only the two first order parameters t and b are relevant; i.e., p=b and $\overline{d}$ cannot be measured. There are, however, tissues which contain a semi-periodic array of specular scatterers at some spacing d resolvable by the ultrasonic imaging device but not detectable in the image by the human observer due to the image texture noise.

Figure 2:
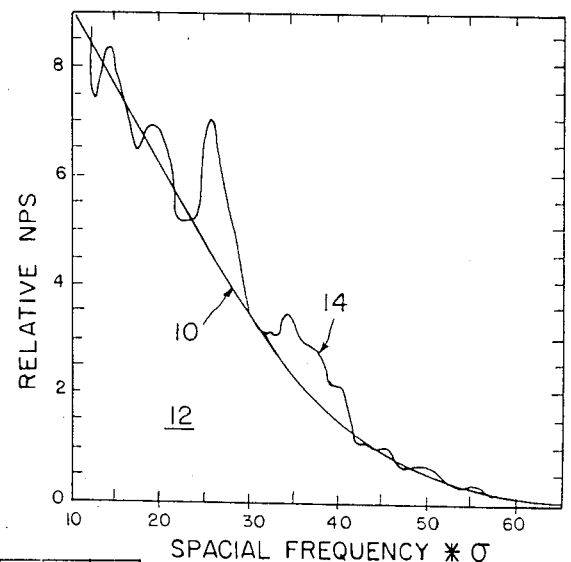
FIG. 2. is a graph which illustrates the average power spectrum, and in which the area 12 below the curve 10 indicates the Rician noise contribution to the image variance, and $\bar{d}$ a fourth texture parameter is specified by the inverse of the spatial frequency of peaks 14 in the power spectrum.

It is difficult to measure the height p (peak) in $R_I(\overline{d})$ because, for most soft tissues, the correlation peaks are small compared to the uncertainty of the measurement and often there is more than one set of semi-periodic structures. A better estimate of p involves partitioning the power spectrum estimate, W(f) (FIG. 2).

$$W(f) = \sigma(f)(I_d + \overline{I_s})^2 + I_d^2 P^*P + <\Delta \widetilde{I_s}^2(f')> + 2I_d P\overline{R}^2 + 2I_d P^* <\Delta \hat{R}(f)>, \quad (8)$$

where $\rho$ and P, $\hat{R}$ and $\overline{R}$, and $I_s$ and $\overline{I_s}$ are Fourier transform pairs.

Figure 3:
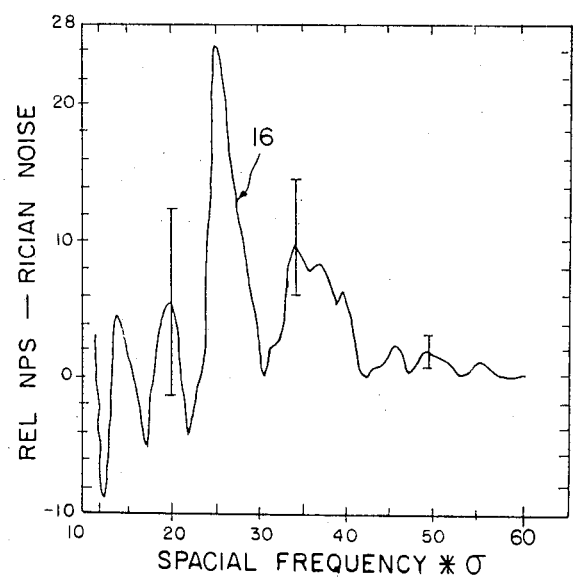
FIG. 3 is a graph 16 showing the power spectrum with Rician noise subtracted and in which error bars denote ± one standard deviation.

Furthermore, we have written $\widetilde{I_s}(f)$ as $\overline{I_s} + \widetilde{\Delta I_s}(f')$, where f' means for all f$\neq$0. We can show that for line spectra, the variance in the specular intensity, the integral of the third term in Eq. 8 over f', can be separated from the rest of the spectrum. In practice, this is done by fitting the spectral minima to a Gaussian function 10, as shown in FIG. 2. The Gaussian function is chosen because the incident pulse has a Gaussian spectrum and because data is processed only along the beam axis. We then subtract the Rician noise 12, the area below the fitted line 10, from the original spectrum 14 and integrate the result (FIG. 3) to obtain the difference quantity p−b.

The scattering quantities t, p, b, and $\overline{d}$ form a four dimensional feature space that is sensitive to changes in tissue microstructure which may result from disease processes and may, therefore, provide diagnostically significant tissue signatures. The analysis has been shown to accurately discriminate among subtle changes in texture that are not easily detected by the human observer.

The structure of a preferred embodiment of a texture discriminator (TD) according to the invention, and its application in an ultrasound B-scanner is discussed in detail below in accordance with FIGS. 4–7.

Figure 4:
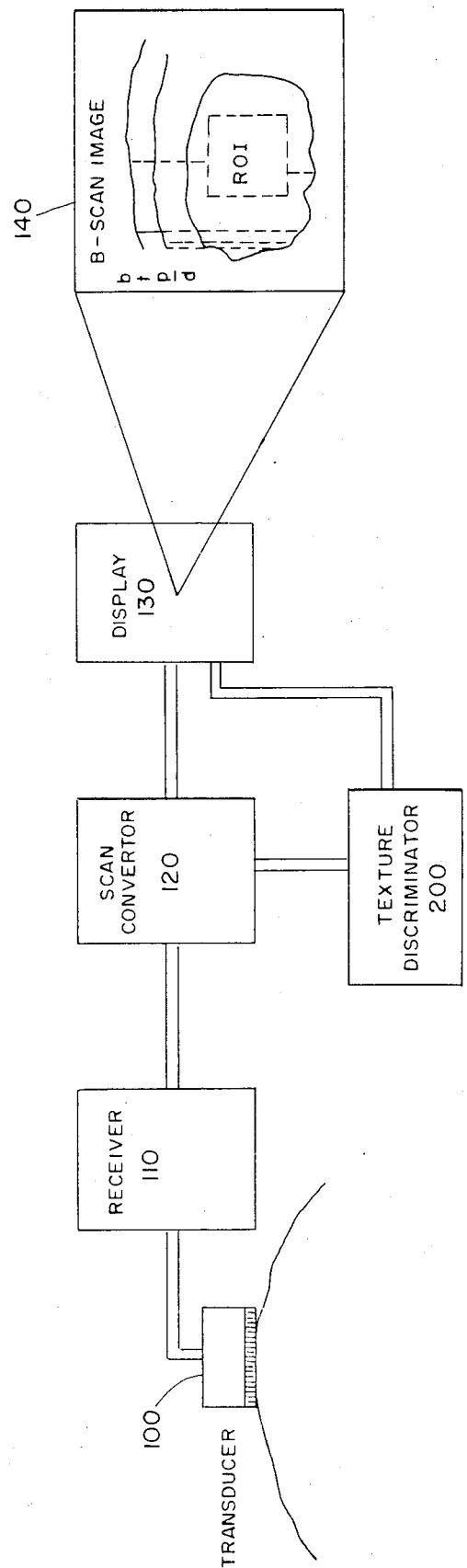
FIG. 4. is a schematic block diagram of a common ultrasound imaging device equipped with a texture dicriminator according to the invention.

FIG. 4 shows a block diagram of a typical ultrasonic B-scanner, in this case a conventional sequential linear array system. The scanner includes a transducer 100, receiver circuitry 110 including any delay line and video processing, a scan convertor 120, the subject texture discriminator 200, and a display monitor 130. The insert 140 for the display monitor illustrates a cross-sectional B-scan in normal rectangular format consisting of many B-mode lines. The image also includes a region of interest as shown by the dashed rectangle. The letters p, t, b and $\overline{d}$ in the upper left corner of the image illustrate the numerical display of the tissue signature variables obtained by the texture discriminator to be described below. Analogous block diagrams would apply for all other clinical ultrasonic B-scan devices including mechanical sector scanners, phased array sector scanners and static compound B-scanners.

In a typical embodiment of the invention, the texture discriminator operates on digital pixel data contained in a region of interest of the conventional B-mode scan convertor. In this preferred embodiment the ROI consists of an N=64 pixel by M=64 pixel area of eight bit image data chosen by the operator from a 512×512 field of view. The image pixel data in the ROI, thus isolated from the original pixel data, is available for transfer to the texture discriminator. The ROI selection is a common feature of commercial ultrasound imaging devices used for length and area calculations, magnification views and prototype attenuation tissue signature measurements. In this embodiment one complete operation of the texture discriminator is carried out in less than 90 msec. Thus display of the tissue signature parameter is updated at a rate of approximately once every three video frames.

The echo signals in the ROI have been processed by the same conventional envelope detection as the B-scan image. The first step of the TD is to square the 2-dimensional array of echo envelope data $x_{ij}$ in the ROI to form a corresponding intensity image of values $I_{ij}=x^2_{ij}$. This is followed by calculation of two first order image statistics b and t $$b = \left[ \sum_{i=1}^{M} \sum_{j=1}^{N} I_{ij} \right]^2 / (MN)^2 \qquad (9)$$

and $$t = \sum_{i=1}^{M} \sum_{j=1}^{N} (I_{ij})^2 / (MN) \qquad (10)$$

To characterize tissues with texture having generalized Rician character, the TD, in parallel with the measurement of b and t, also determines two second order texture statistics from the ultrasound intensity image. These are $\bar{d}$ and p which are obtained from the noise power spectrum (NPS). FIG. 2 shows an NPS 14 from a B-scan of normal human liver obtained by averaging, in the lateral direction, 64 one-dimensional NPS measured from data along the axial direction of a 64×64 ROI.

The average NPS 14 shows several peaks at identifiable spatial frquencies, from which the tissue scatterer average spacing $\bar{d}$ is obtained. The other second order statistical parameter measured by the texture discriminator is p, the variance of ultrasonic backscatter intensity due to the ordered tissue structure discussed above. p−b is obtained from the NPS by numerically separating the Rician noise 10 contribution to the NPS 14 from the variance in the specular intensity. Curve 10 illustrates the Rician noise component which is removed so that a resulting summation of the net NPS 16 (FIG. 3) yields the described parameter p−b.

The four parameters t, p, b and $\bar{d}$ uniquely specify the acoustic characteristics of the tissue in the defined ROI for medical diagnosis. The details of the on-line measurement of these variables in the texture discriminator will now be described.

Figure 5:
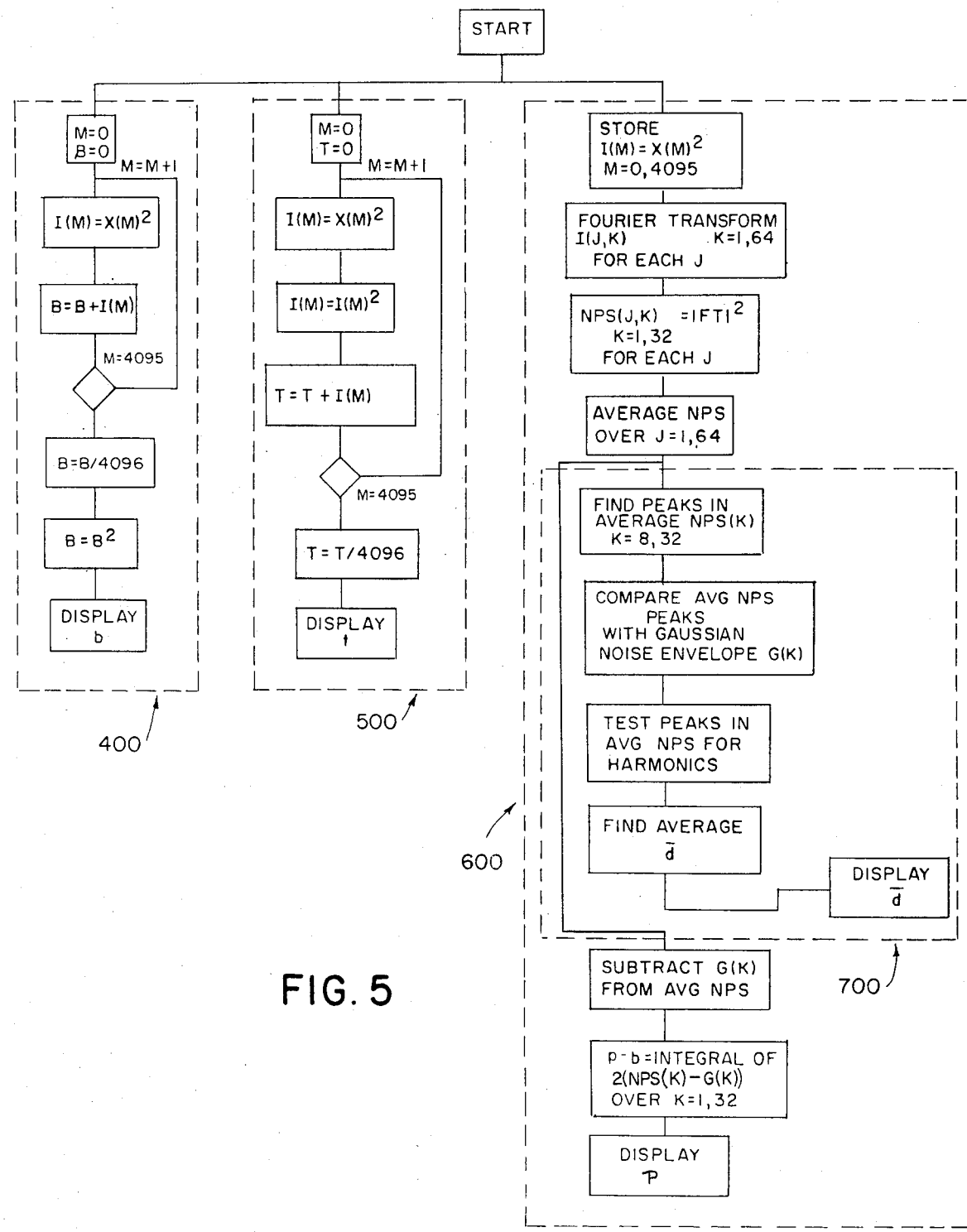
FIG. 5. is a three section flow chart outlining the process of obtaining first and second order statistics of the scanned region of interest ROI.

The operation of the texture discriminator (TD) 200 of FIG. 4 in determining b is illustrated further in FIG. 5. The flow chart 400 which shows the b measurement includes the squaring of the pixel data, x(m), the accumulated sum of the intensities and the final scaling and squaring to obtain b.

The flow chart 500 of FIG. 5 shows the t measurement which includes raising the pixel data x(m) to the fourth power $I^2(m)$, the summing operation, and the final averaging to obtain t. Similarly higher moments of the first order statistics such as variance or kurtosis can be determined and displayed by analogous high speed digital operations.

Figure 6:
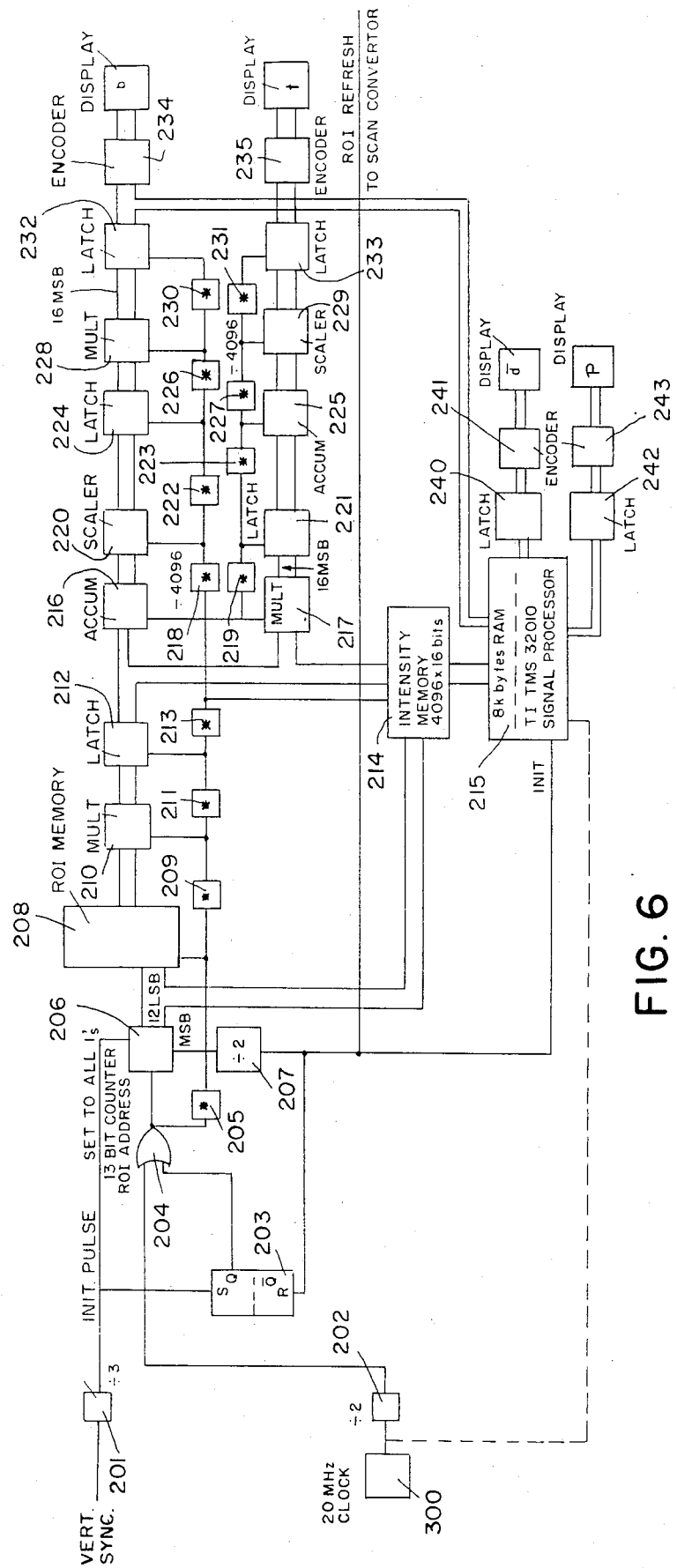
FIG. 6 is a schematic block diagram of a preferred embodiment of the present invention.

FIG. 6 is a schematic of the texture discriminator (TD). In this preferred embodiment, the ROI feature of a conventional ultrasound scanner is assumed to operate continually so that the image pixel data within the ROI is stored in its own ROI memory 208 and is updated by conventional means every three video frames or 10 updates/second for a conventional 30 frame per second real time ultrasound imaging device. The TD is initiated with the reception of a vertical sync pulse from the TV sync generator which is used to synchronize conventional scanners. The vertical sync pulse passes through a ÷3 counter 201 so that the TD is initialized 10 times per second. The Init pulse sets the 13 bit ROI address counter 206 to all 1's. The Init pulse also sets flip-flop 203 whose Q output is one input to And gate 204.

The operation of the TD is paced by a 20 MHz master clock 300 resulting in a pulse rate of one pulse per 50 nsec. The output of the master clock 300 passes through the ÷2 counter 202 and then forms the other input to And gate 204. Thus after the Init pulse, the output of And 204 increments the 13 bit ROI address counter 206 every 100 nsec. The most significant bit (MSB) of the counter 206 passes to the ÷2 counter 207.

The 13 bit ROI address counter 206 is incremented every 100 nsec. The 12 least significant bits of the address counter 206 determine the memory address of the 4096×8 bit ROI memory 208 which contains the ultrasound pixel data for the 64×64 ROI. The counter 206 also determines the address for the 4096×16 bit intensity memory 214. The ROI memory 208 is also cycled by the output of And 204 after a delay 205. Each eight bit pixel is then transferred in turn to both inputs of multiplier 210 to obtain the square of the pixel data, multiplier 210 in turn is cycled after the delay 209, and the 16 bits of the pixel intensity word is transferred to latch 212.

Latch 212 is cycled after delay 211, and the pixel intensity word is transferred to three destinations simultaneously: accumulator 216, multiplier 217 and the correct address of the intensity memory 214. The intensity data is summed in accumulator 216 with each count of the 12 bit ROI address counter 206 as delayed by delay 213. When the counter 218 reaches 4095, the accumulated sum is passed to scaler 220 which forms a mean value of the backscattered ultrasound intensity and then to latch 224 after delay 222. The data is then sent to multiplier 228 after a delay 226 to form the mean intensity squared. Finally, this value is sent to latch 232 after a delay 230 and then to the digital encoder 234 for display. The b value is also sent to the signal processor 215 for later use.

In the parallel operation for the t parameter, the output of latch 212 passes to multiplier 217, after delay 213, to from the square of each intensity pixel. This data passes to latch 221 after delay 219 and then to accumulator 225 after delay 223 to form the sum. When the address count counter 227 reaches 4095 the sum is passed to scaler 229 to form a mean and then to latch 233 after delay 231 and then to encoder 235 to form the t display.

In the third parallel operation the pixel intensity data from latch 212 is loaded into the intensity memory 214, which is cycled after delay 213. These three parallel operations consume 409.6 μsec so that the b and t parameters are displayed at that time.

When the counter 206 reaches the count of 4096, at which point all the pixels are retrieved, the most significant bit (MSB) of the counter 206 passes to the ÷2 counter 207. The output of the ÷2 counter 207 resets flip-flop 203 so that its Q output is "low", disabling And gate 204 and thus holding the b and t values. The output of the ÷2 counter 207 also is sent to the signal processor 215 initiating the signal processor 215 operations, explained below, to determine the $\bar{d}$ and p parameters. The final value of the $\bar{d}$ parameter measured in signal processor 215 is transferred to latch 240 and then to digital encoder 241 for the display. The parameter p, which is also measured in signal processor 215, is passed to the latch 242 and then to encoder 243 for display.

Figure 7:
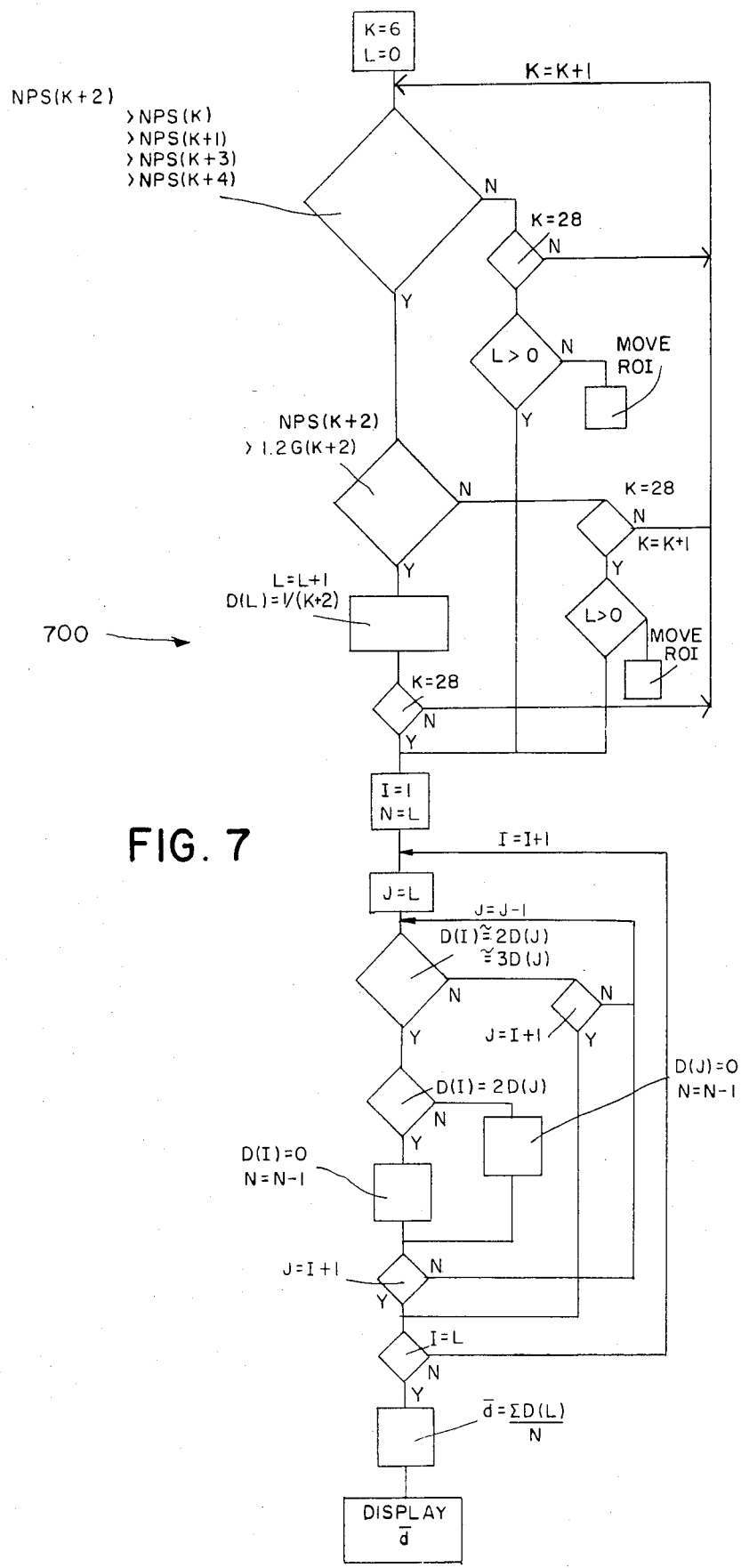
FIG. 7 is detailed flow chart of a process of measuring second order statistics of a texture discriminator of the present invention as shown in block 700 of FIG. 5.

Referring to FIGS. 5–7, the operation of signal processor 215 is explained in detail. The output of the ÷2 counter 207 initiates a Fourier transform (FT) operation in signal processor 215. The FT pulse is also passed to the scan convertor 120 of FIG. 4 to initiate updating of the ROI memory 208 for the next video frame. A 64 sample FT is performed in the axial direction for each of the 64 intensity lines in the intensity memory 214 corresponding to the 64 B-mode lines in ROI. The initial 64 pixel intensity line is read from the intensity memory 214 into the random access memory (RAM) of the signal processor 215. The resulting complex FT is squared to obtain a 32 sample NPS and then stored in the RAM for subsequent averaging. The 64 FT's are performed sequentially, the resulting NPS's are accumulated in memory and then scaled to obtain an average NPS in the axial direction of the ROI. The elapsed time to perform these operations is approximately 41 msec.

Following the determination of the average NPS of the image ROI, additional signal processing functions are performed to obtain the parameters $\bar{d}$ and p as shown in FIG. 5 in the flow path 600 and in FIG. 7. By conversion of the algorithm to assembly language, this additional, non-FT signal processing will consume approximately 46 msec per ROI. The 32 sample average NPS is scanned to find the location of any local peaks as shown in the example average NPS of FIG. 2. The height of each detected peak in the average NPS is then compared to a Gaussian noise function G(K), K=1,32 stored in a look-up table in the memory of the signal processor 215 illustrated by the curve 10 in FIG. 2. The Gaussian noise function is precalculated based on conventional speckle size theory and the impulse response of the ultrasound transducer. If a detected peak in the NPS exceeds 120% of the Gaussian noise function, the sample location of the peak (K=8,32) is stored. Next, the spatial frequency location of each unique NPS peak is converted to a spatial length via a look-up table contained in memory, which includes a scaled inverse of the samples K=8,32. The sample locations of each peak are then tested for redundancy, i.e., the presence of harmonics or subharmonics. The locations of only unique peaks are averaged to obtain the average interscatterer spacing $\bar{d}$.

Subsequently, the Gaussian noise envelope G(K) is subtracted from the average NPS(K). The net values of the difference function are accumulated forming an equivalent integral of the area under the tissue structure peaks. The b value from latch 232 is then added to this integral then scaled to form the parameter p.

An alternative method for determining the noise envelope, which need not depend on the pre-calculated spectral characteristics of the individual transducer, is to fit a Gaussian function to the minima of the average NPS. The function is then subtracted from the NPS to determine p.

In this preferred embodiment of texture discriminator, it is assumed that the original 512×512 pixel image is obtained over a maximum range of 20 cm and is digitized in the scan convertor so that a 64×64 ROI results in a sample of approximately 25 mm×25 mm. Thus, a 64 sample FT yields and NPS of 32 unique values and a spatial frequency resolution of 0.04 mm$^{-1}$. This yields a useful range to search for average tissue scatterer spacing of 0.8 to 3.1 mm, which lies within the axial resolution limits of a conventional 3.5 MHz abdominal or cardiac transducer.

In one embodiment, the Fourier transform is carried out using the commercially available Texas Instrument TMS32010/20 digital signal processor (including 8 kB of external memory for the TMS32010 and 256 kB for the TMS32020) which obtains a 64 sample FT in 0.63 msec. The TMS32010/20 uses a 20 MHz clock which is synchronized with the master clock.

The peak detection routine is limited from sample 8 to 32 to adhere to the spatial frequency limitation described above.

The total elapsed time for measurement of t, p, b and $\bar{d}$ is less than 90 msec. With the reception of the next television vertical sync pulse, from the ÷3 counter 201, flip-flop 203 is set again, and the texture discriminator is reset for operation.

In certain alternative embodiments, the texture discriminator includes measurement of the second order statistical parameters in the lateral direction. Furthermore, measurements can be made of higher order statistics using analogous designs. Also, second order statistical measurements can be obtained from the autocorrelation function (ACF) the Fourier transform of the NPS. Furthermore, implementation of high speed on-line matched filters can be included to eliminate non-Gaussian interference such as that due to blood vessels. Analogous hardware and standard algorithms can be used to implement, on-line and at high speed, other texture analyses such as cepstra and pattern recognition techniques such as the co-occurrence matrix. Finally analogous hardware and standard algorithms can be used to process the radiofrequency echo signal or the B-mode echo envelope signals instead of the intensity echo signal as described above. In each of these alternatives, multiple signal processing paths can be performed in parallel to increase speed.

Another feature of the TD is to store the ROI pixel data using the freeze frame option of the imaging device and then determine the tissue signature parameter at a slower rate. The advantage of this freeze frame implementation is that only data within a given frame is analyzed. This allows analysis of cardiac muscle, for example, that would normally be moving in and out of an ROI in real time. Of course, other various sizes and shapes of the ROI can also be used with corresponding longer or shorter operation times of the TD for any given examination.

The foregoing description of the principle and the specific embodiments will so fully reveal the general nature of the invention that others can, by applying current and disclosed knowledge, readily modify and-/or adapt the disclosed embodiments for various implementation and/or other pertinent applications without departing from the generic concept. Therefore, such adaptations and modifications should and are intended to be comprehended within the meaning and scope of the disclosed embodiments.

It is also possible to carry out the invention by measuring other second order parameters, on-line and at high speed, such as cepstra and pattern recognition variables, e.g. run length statistics, co-occurrence matrices, "entropy".

What is claimed is:

1. A method for classifying a region of interest (ROI) within a portion of a body using at least two statistical properties of ultrasound echoes from said ROI, and for forming an image of said portion of said body with said ROI, said statistical properties being related to physical scattering properties of said ROI, said method comprising creating said image by emitting at least one burst of ultrasound energy with a piezoelectric transducer into said body, including into said portion of said body and said ROI therein, and receiving with transducer means said ultrasound echoes from respective parts of said ROI and other ultrasound echoes from respective parts of the rest of said portion of said body, as acoustic reflections of each said at least one burst from respective parts within said portion of said body and said ROI, said transducer means outputting a plurality of electrical signals respectively corresponding to said acoustic reflections from said respective parts within said portion of said body, amplifying said electrical signals output from said transducer, and using the respective amplified electrical signals from each said burst to create said image, determining, for said classifying of said ROI with said using of said at least two statistical properties, at least two of:

(a) a first order statistical parameter b indicating the square of the mean of intensities of all of said ultrasound echoes from said ROI for each respective burst, each said intensity being proportional to the square of the envelope of the respective ultrasound echo;

(b) a first order statistical parameter t, wherein said parameter t is a variance in said intensities of said ultrasound echoes from said ROI plus a sum of a total average of said backscatter intensity in said ROI;

(c) a second order statistical parameter $\bar{d}$, wherein said parameter $\bar{d}$ is a measure of average spacing of any periodic and semi-periodic array of specular scatterers in said ROI, said statistical parameter $\bar{d}$ corresponding to an average spatial frequency location of non-redundant peaks of a noise power spectrum corresponding to the square of the absolute magnitude of a Fourier transformation of said intensities of said ultrasound echoes from said ROI; and (d) a second order statistical parameter p, said statistical parameter p being determined only in the event said statistical parameter b is determined as one of said at least two statistical parameters, wherein said statistical parameter p is the variance of said backscatter intensity due to said periodic and semi-periodic array in said ROI plus the sum of the total average of said backscatter intensity from said ROI, said statistical parameter p being formed by integration of a remainder of said noise power spectrum after subtraction of a Gaussian noise envelope term therefrom, and by then subtracting said statistical parameter b from the integrated remainder; and displaying at least two values, each corresponding to at least one respective one of said at least two statistics parameters;

wherein said at least two displayed values allow said classifying based on physical characteristics of said ROI, including whether the material in said ROI in said body is in a normal or abnormal state.

2. The method of claim 1, comprising use of a plurality of said bursts for providing respective ones of said ultrasound echoes for said determining of said statistical parameters, and wherein each said determined parameter $\bar{d}$ is obtained from an average noise power spectrum.

3. The method of claim 1, wherein each said statistical parameter is determined with respect to a range direction of a scanning beam for providing each said burst and said ultrasound echoes, said ROI having a corresponding depth in said range direction.

4. The method of claim 1, comprising use of a plurality of said bursts, wherein each said determined statistical parameter is with respect to a lateral direction transverse to a direction of propagation of said bursts.

5. The method of claim 1, wherein each said parameter $\bar{d}$ and said parameter p that is determined corresponds to an autocorrelation function of said intensities.

6. The method of claim 1, comprising eliminating non-Gaussian interference due to blood vessels in said ROI to increase accuracy of said determining of each said at least two statistical parameters b, t, $\bar{d}$ and p.

7. The method of claim 1, comprising freezing said image of said ROI for determining at a slower rate each of said at least two statistical parameters for said ROI, and for analysis of material moving in said ROI.

8. The method of claim 1, wherein all of said statistical parameters b, t, $\bar{d}$, and p are determined for each said ROI.

9. A device for performing the method of claim 1, comprising:

memory means for storing data including pixel data of said image, each said pixel data being the magnitude of the envelope of a respective one of said ultrasonic echoes and means for squaring said pixel data, wherein said squared data is also stored in said memory means, and two of said statistics parameters are determined by said processing means from said squared data.

10. The method of claim 1, comprising using an average of a plurality of noise power spectra including said noise power spectrum, for said determining of said at least two statistics parameters, when said at least two determined statistical parameters include at least one of said statistical parameters $\bar{d}$ and p.

11. The method of claim 1, comprising performing on-line in real time said determining of said at least two statistical parameters and said displaying of said at least two respective values, for successive displaying of ultrasound images including said ROI with successive displays of said at least two respective values, for said classifying of the body under investigation within each said ROI.

12. A texture discriminator device for classification of texture of an ultrasound image in a body under investigation for any selected region of interest (ROI), comprising:

a master clock for determining pace of operation of the texture discriminator, an ROI memory for storing pixel data of said image from within said region of interest, and means for updating said ROI memory under control of said master clock, an ROI address counter to determine the memory address of said ROI memory for retrieval and renewal of contents of said ROI memory, means for squaring said pixel data stored by said ROI memory and means for transmission of said squared data for further processing, an intensity memory wherein the squared data are stored for further processing, a signal processor for determining at least two of four statistical parameters b, t, $\bar{d}$ and p from said data stored in said intensity memory for said ROI, and means for displaying at least two respective values for analysis of normal and abnormal states of constituent matter in said ROI, each said respective value corresponding to at least one respective one of said at least two statistical parameters, wherein;
said parameter b corresponds to a squared mean of intensity of said image and represents a measure of mean ultrasound backscatter intensity;

said parameter t corresponds to a variance in the intensity image plus a sum of a total average of said backscatter intensity;

said parameter $\bar{d}$ corresponds to a measure of average spacing of any periodic and semi-periodic array of tissue specular scatterers and is obtained from an average spatial frequency location of non-redundantpeaks of a noise power spectrum of said ROI; and said parameter p corresponds to the variance of said backscatter intensity due to said periodic and semi-periodic tissue array plus the sum of the total average of said backscatter intensity, and is obtained by integrating the remainder of said noise power spectrum after subtraction of a Gaussian noise envelope term therefrom, and by then subtracting the parameter b from the integrated remainder.

13. The texture discriminator of claim 12, wherein said signal processor comprises:

means for high speed implementation of a Fourier transform, to obtain said noise power spectrum for determining said parameter d and said parameter p, for determining said Gaussian noise envelope to be subtracted from said noise power spectrum for determining said parameter p from said noise power spectrum and said parameter b; and a memory means for storing interstage measurements and a predetermined Gaussian noise function corresponding to said Gaussian noise envelope.

14. The texture discriminator of claim 13, comprising means for retrofittedly connecting said texture discriminator to a medical ultrasound B-scan system.

15. The texture discriminator of claim 12, comprising means for eliminating non-Gaussian interference for high speed analysis for said classifying of said matter in said ROI.

16. The texture discriminator of claim 12, comprising means for selective freeze frame operation of said image to allow said analysis of matter that moves in and out of said ROI in real time.

17. The texture discriminator of claim 12, comprising means for selectively varying the size and shape of said ROI.

18. A method for classifying a region of interest (ROI) within a portion of a body using at least two statistical properties of ultrasound echoes from said ROI, and for forming an image of said portion of said body with said ROI, said statistical properties being related to physical scattering properties of said ROI, said method comprising creating said image by emitting at least one burst of ultrasound energy with a piezoelectric transducer into said body, including into said portion of said body and said ROI therein, and receiving with transducer means said ultrasound echoes from respective parts of said ROI and other ultrasound echoes from respective parts of the rest of said portion of said body, as acoustic reflections of each said at least one burst from respective parts within said portion of said body and said ROI, said transducer means outputting a plurality of electrical signals respectively corresponding to said acoustic reflections from said respective parts within said portion of said body, amplifying said electrical signals output from said transducer, and using the respective amplified electrical signals from each said burst to create said image, determining, for said classifying of said ROI with said using of said at least two statistical properties, at least two of:

(a) a first order statistical parameter b indicating the square of the mean of intensities of all of said ultrasound echoes from said ROI for each respective burst, each said intensity corresponding to the square of the envelope of the respective ultrasound echo;

(b) a first order statistical parameter t indicating the mean of the squares of all of said intensities of said ultrasound echoes from said ROI;

(c) a second order statistical parameter $\bar{d}$ indicating an average spacing of any periodic and semi-periodic array of specular scatterers in said ROI, said parameter $\bar{d}$ being obtained from non-redundant peaks of a noise power spectrum corresponding to a squared Fourier transformation of said intensities of said ROI; and (d) a second order statistical parameter p corresponding to the integral of a remainder of a subtraction of a Gaussian noise envelope from said noise power spectrum, less said statistical parameter b; and displaying at least two values, each corresponding to at least one respective one of said at least two statistical parameters;

wherein said at least two respective displayed values allow said classifying of the tissue of said region of interest in said portion of said body as being in normal and abnormal states.

19. The method of claim 18, wherein
a plurality of said bursts of ultrasound are provided for said classifying of said ROI within said portion of said body under investigation, to produce respective ones of said ultrasound echoes with each said ultrasound echo corresponding to a respective position within said body including said ROI, said image is formed by displaying a data corresponding to each said ultrasound echo at a respective position of the image, and said determining of said second order statistical parameter $\bar{d}$ is based on an average of noise power spectra including said noise power spectrum, each said noise power spectrum being provided by a respective square of a Fourier transformation of respective ultrasound echoes from respective positions within said body for each respective one of said plurality of bursts.

20. The method of claim 18, wherein
a plurality of said bursts of ultrasound are provided for said classifying of said ROI within said proportion of said body under investigation, to produce respective ones of said ultrasound echoes with each said ultrasonic echo corresponding to a respective position within said body including said ROI, said image is formed by displaying a data corresponding to each said ultrasonic echo at a respective position of the image, and said Fourier transform, the square of which is used to provide said statistical parameter $\bar{d}$, is of a plurality of respective intensities from different ones of said bursts, corresponding to respective ultrasound echoes from respective points in said portion of said body with said ROI which are aligned largely transversely to the respective ones of said points corresponding to any one of said bursts.

* * * * *